(12) United States Patent
Ehleringer et al.

(10) Patent No.: US 9,810,673 B1
(45) Date of Patent: Nov. 7, 2017

(54) CANNABIS CULTIVATION TEST

(71) Applicants: James Ehleringer, Salt Lake City, UT (US); Lesley Chesson, Salt Lake City, UT (US); Rozann Dunn, Salt Lake City, UT (US); Joshua Ehleringer, Salt Lake City, UT (US); Patrick Shea, Salt Lake City, UT (US); Brett Tipple, Salt Lake City, UT (US)

(72) Inventors: James Ehleringer, Salt Lake City, UT (US); Lesley Chesson, Salt Lake City, UT (US); Rozann Dunn, Salt Lake City, UT (US); Joshua Ehleringer, Salt Lake City, UT (US); Patrick Shea, Salt Lake City, UT (US); Brett Tipple, Salt Lake City, UT (US)

(*) Notice: Subject to any disclaimer, the term of this patent is extended or adjusted under 35 U.S.C. 154(b) by 0 days.

(21) Appl. No.: 15/491,336

(22) Filed: Apr. 19, 2017

Related U.S. Application Data

(60) Provisional application No. 62/324,500, filed on Apr. 19, 2016.

(51) Int. Cl.
| | | |
|---|---|---|
| G06F 17/00 | (2006.01) | |
| G06F 17/10 | (2006.01) | |
| G06F 19/00 | (2011.01) | |
| G01N 33/00 | (2006.01) | |
| G01N 33/15 | (2006.01) | |
| C12M 1/34 | (2006.01) | |
| G01N 33/18 | (2006.01) | |
| G01N 30/88 | (2006.01) | |
| G01N 33/94 | (2006.01) | |

(52) U.S. Cl.
CPC ..... *G01N 33/0098* (2013.01); *G01N 33/0036* (2013.01); *G06F 19/707* (2013.01); *G01N 33/0047* (2013.01); *G01N 33/1846* (2013.01); *G01N 33/948* (2013.01); *G01N 2030/8868* (2013.01); *G01N 2333/415* (2013.01); *G01N 2458/15* (2013.01); *G01N 2560/00* (2013.01)

(58) Field of Classification Search
CPC .......... G01N 33/0098; G01N 33/1846; G01N 33/0036; G01N 33/0047; G01N 33/948; G01N 2030/8868; G01N 2458/15; G06F 19/707

See application file for complete search history.

(56) References Cited

U.S. PATENT DOCUMENTS

2017/0059480 A1\* 3/2017 Hsiung ................. G06F 19/703

OTHER PUBLICATIONS

Farquhar et al, "On the Relationship between Carbon Isotope Discrimination and the Intercellular Carbon Dioxide Concentration in Leaves",. Aust. J. Plant Physiol., 1982, vol. 9, pp. 121-137, (Year: 1982).\*

(Continued)

*Primary Examiner* — Jennifer Wecker
(74) *Attorney, Agent, or Firm* — Parsons Behle & Latimer

(57) ABSTRACT

Systems and methods are disclosed to determine that a *cannabis* plant has been cultivated under desired cultivation conditions. Quantitative processes are disclosed, based on stable carbon isotope ratio analysis, and using modeling constraints and Bayesian approaches to produce a likelihood that a *cannabis* plant was cultivated under desired conditions (e.g., indoors), and provide a quantitative estimate of the average $CO_2$ concentration in the growth environment.

16 Claims, 3 Drawing Sheets

(56) References Cited

OTHER PUBLICATIONS

Tricia N. Denton, et al., Natural Abundance of Stable Carbon and Nitrogen Isotopes in Cannabis Sativa Reflects Growth Conditions, 28 Aust J. Plant Physiol., 1005-1012 (2001).
Farquhar et al; On the Relationship between Carbon Isotope Discimination and the Intercellular Carbon Dioxide Concentration in Leaves; p. 121-137 1982.
Amanda L. Booth, et al., Tracing Geographic and Temporal Trafficking Patterns for Marijuana in Alaska Using Stable Isotopes (C, N, O and H), 202 Forensic Sci. Int'l., 45-53 (2010).
Farquhar et al; Carbon Isotope Discrimination and Photosynthesis; p. 503-537 1989.
Jason B. West, et al., Stable Isotope Ratios of Marijuana. I. Carbon and Nitrogen Stable Isotopes Describe Growth Conditions, 54, No. 1, J. Forensic Sci., 84-89 (Jan. 2009).

* cited by examiner

CANNABIS CULTIVATION TEST

CROSS-REFERENCE TO RELATED APPLICATIONS

This application, under 35 U.S.C. §119, claims the benefit of U.S. Provisional Patent Application Ser. No. 62/324,500 filed on Apr. 19, 2016, and entitled "*Cannabis* Indoor Cultivation Test," the contents of which are hereby incorporated by reference herein.

FIELD OF THE DISCLOSURE

The disclosure relates generally to systems and methods for determining the cultivation conditions of *cannabis* plant material. In particular, the disclosure relates to systems and methods for implementing a stable isotope test to determine the cultivation conditions of *cannabis* plant material.

BACKGROUND

There is a legal and regulatory need to impartially determine, certify, or verify that a *cannabis* plant, or *cannabis* product, was produced under certain cultivation conditions. For example, currently, almost all states within the United States where *cannabis* is legal (typically as "medicinal marijuana"), 20 of 23 states (as of January 2016) require that the *cannabis* be cultivated indoors. These regulations occur at both the state and municipal levels. Yet at present there are no quantifiable tests or processes in the marketplace that can confidently identify a *cannabis* plant that has been cultivated indoors versus a *cannabis* plant that was cultivated outdoors.

The existing need is for an independent, analytical, and reliable test that is based on a combination of quantitative measurements and statistical analyses, and that is not a test based on either personal, experiential observations, or an approach that relies on the use of printed labels attached to the plant. One advantage of an analytical and quantitative measurement approach is that it can be conducted by many analytical facilities to reach the same conclusion and to ensure reliable quantitative results, independent of the analyst or laboratory. This is the kind of testing approach called for by the National Research Council. In contrast, experiential observations can be subject to personal judgment biases and influenced by the depth of the analyst's experience, leading to different and often conclusions. Labels (e.g., tags, bar codes, RFID chips) attached to plants offer no guarantee that the material has been indeed cultivated indoors. Indeed such labels can be added afterward to a *cannabis* plant cultivated under either indoor or outdoor conditions, especially when a chain-of-custody process is not in place.

At present there are no reliable analytical tests available to determine, certify, or verify that a plant or plant product had been produced as a result of determinable cultivation conditions. For example, there are currently no available tests or processes to reliably and quantitatively indicate that a plant was cultivated indoors. The present disclosure provides new, quantitative, and reliable tests or processes to verify, certify, and proclaim that *cannabis* was cultivated under determinable conditions, such as indoors, as required by state laws and regulations.

Stable isotopes at natural abundance levels are nature's recorders, storing aspects of the environmental conditions in the organic compounds within the plant, plant organs, and plant compounds. Historically, stable isotopes at natural abundance levels have been used to source the origins of controlled substances, such as cocaine and heroin. Recent studies of stable isotope abundances—measured as ratios—in *cannabis* have been used to source the cultivation conditions and origins of the *cannabis*. While three publications have noted that *cannabis* plants cultivated indoors could be distinguished from *cannabis* plants cultivated outdoors, none of these studies developed the analytical tools or unbiased processes to reliably categorize plant cultivation conditions. The three publications are: Tricia N. Denton, et al., *Natural Abundance of Stable Carbon and Nitrogen Isotopes in Cannabis Sativa Reflects Growth Conditions*, 28 Aust. J. Plant Physiol., 1005-1012 (2001); Jason B. West, et al., *Stable Isotope Ratios of Marijuana. I. Carbon and Nitrogen Stable Isotopes Describe Growth Conditions*, 54, no. 1, J. Forensic Sci., 84-89 (January 2009); and Amanda L. Booth, et al., *Tracing Geographic and Temporal Trafficking Patterns for Marijuana in Alaska Using Stable Isotopes* (C, N, O and H), 202 Forensic Sci. Int'l., 45-53 (2010), each of which is incorporated herein by reference. Instead, each of these studies simply placed *cannabis* plants into an indoor versus outdoor classification based on an arbitrary threshold isotope value. Other drawbacks of existing identification processes also exist.

Disclosed herein are systems and processes that rely on different theoretical framework for interpreting stable isotopes ratios, network analyses, and Bayesian interpretations to certify the likelihood that the *cannabis* had been cultivated under determinable conditions, such as indoors, and provide a quantitative measure of the average indoor $CO_2$ concentration during plant growth. Other advantages also exist.

SUMMARY

As used herein, "*cannabis*" means the leaf, stem, seed, root, a specific compound from, flower parts of, and/or any product from a *Cannabis* species (e.g., *Cannabis sativa* L., *Cannabis indica* Lam., *Cannabis ruderalis* Janish.), and includes both "marijuana" and "hemp," two genetically distinct forms of *cannabis* that are distinguished on the basis of the relative abundances of different cannabinoids, as well as any variety of the above species, cultivar of the above species, or hybrid between the above species.

The terms "bulk plant material" refers to different plant parts (i.e., organs) be they intact or ground. Bulk plant material may consist of any combination of leaves, seeds, flowers, stems, roots, and the like from a *cannabis* plant.

The terms "cultivation condition" refers generally to the conditions under which a plant is grown. As used herein, cultivation condition means the environment in which a plant is grown (e.g., indoors, outdoors, etc.), the farming practice (e.g., intensive, hobby, hydroponic, aeroponic, etc.), the geographical location in which a plant is grown (e.g., California, Colorado, etc.), the ecosystem in which a plant is grown (e.g., forest, desert, riparian, etc.), the soil conditions in which a plant is grown (e.g., alkaline, acidic, etc.), the water stress level in which a plant is grown, or the like.

The terms "indoor cultivation" or "cultivated indoors" mean cultivation in any enclosed space used for plant cultivation, including, but not limited to, greenhouses, glass houses, hot houses, buildings, warehouses, or similar enclosed structures. Thus, indoor cultivation is the growth location of plants in an environment where the indoor air supplies are fully or partially isolated from outside air. Indoor air spaces may or may not be directly connected to outside air through openings and/or ventilation systems.

The terms "outdoor cultivation" or "cultivated outdoors" mean cultivation in any unenclosed space used for plant cultivation, including, but not limited to, fields, pastures, farms, gardens, and the like. Thus, outdoor cultivation or cultivated outdoors are the growth location of plants in an environment where the air supplies are fully utilizing only outside air from the atmosphere.

A "nuclide" is defined herein as an atomic species containing a specific number of protons and neutrons within its nucleus. An "element" is a nuclide defined herein by the number of protons within its nucleus. A "stable isotope" is defined herein as a nuclide that does not undergo radioactive decay over time, but persists in the same configuration with respect to the number of protons and neutrons within the nucleus. The terms "stable isotopes" refers herein to multiple nuclides of the same element. For example, the element carbon has two stable nuclides: $^{12}C$ and $^{13}C$, each with six protons but one nuclide ($^{12}C$) having six neutrons while the other nuclide ($^{13}C$) contains seven neutrons.

As used herein, the terms "stable isotope ratio" are terms that describe the relationship of the ratio of the molar abundances of the heavy-to-light stable nuclides of an element in a substance (solid, liquid, or gas; pure, or a mixture) relative to the ratio of the molar abundances of the heavy-to-light stable nuclides of an element in an internationally accepted standard reference material. Specifically, the stable isotope value is defined in "delta notation" ($\delta$) as:

$$\delta = (R_{sample}/R_{standard} - 1),$$

where $R_{sample}$ is the molar abundances of the heavy-to-light stable nuclides of an element in the sample and $R_{standard}$ is the molar abundances of the heavy-to-light stable nuclides of an element in an internationally recognized standard. These $\delta$-values are typically small numbers and are often presented in multiples of $10^{-3}$ or parts per thousand ("per mil," symbol ‰). As disclosed herein, the carbon isotope ratio ($\delta^{13}C$) is utilized, where R refers to $^{13}C/^{12}C$. For carbon isotope values, the international standard is Vienna Pee Dee Belemnite (VPDB), which has a $^{13}C/^{12}C$ ratio of 0.0112372. The International Atomic Energy Agency (IAEA), or the U.S. National Institute of Standards and Technology (NIST), or the like, distributes VPDB to analytical laboratories.

As used herein, the term "isotope ratio mass spectrometer (IRMS)" is the name applied to specialized and commercially available instruments for the measurement of carbon isotope ratios in a sample and its comparison to international standards. Commercially available combustion devices are coupled to the IRMS to facilitate conversion of a sample from its original organic form into gases that are analyzed by the IRMS.

The terms "likelihood ratio" means a statistical evaluation of the ratio of the probability that a measurement observation could have occurred as a result of plant cultivation under one set of cultivation conditions to the probability that a measurement observation could have occurred as a result of that plant's cultivation under different cultivation conditions.

The term "database" means an accumulation of authentic measurements or observations and associated metadata. The term "model" means any mathematical construction of a relationship among different variables.

The terms "measure," "measured," and "measurement" mean any analytical process that provides quantitative evaluations on the identity, quantity, and/or abundance of a substance or mixture of substances. As used herein, a measurement is meant to include stable isotope ratio measurements.

The terms "determine," "determined," and "determination" mean establishing or ascertaining a conclusion based on an analytical measurement or a combination of analytical measurements on a sample material. The terms "verify," "verified," and "verification" mean a conclusion that a determination is true, justified, and accurate. A "verification" is based on the application of measurements, likelihood ratio analyses, and evaluations in comparison to observations in a database. The terms "certify," "certified," or "certification" means a confirmation that a determination has been verified.

Accordingly, disclosed embodiments include a *cannabis* cultivation condition determination system comprising an isotope measurement portion for measuring a carbon isotope value of a *cannabis* sample, and a computational portion further comprising a processor and a database comprising authentic material carbon isotope values. As disclosed, the processor executes one or more programs to classify the measured carbon isotope value of the *cannabis* sample against one or more threshold criteria relating to the likelihood of being cultivated under specific conditions. In addition the processor executes one or more programs to evaluate whether the measured carbon isotope value is above or below the one or more threshold criteria. In addition the processor executes one or more programs to further classify a below-threshold measured carbon isotope value by comparing a probability density function describing the authentic material carbon isotope values, and, based on the comparison, determines a below-threshold likelihood ratio that the below-threshold measured carbon isotope value is consistent with the likelihood the cultivation condition has occurred.

In further embodiments, the system may include a sample preparation portion for preparing the *cannabis* sample for measurement in the isotope measurement portion.

Further embodiments of the system may also include a certification portion for certifying that the cultivation condition has, or has not, occurred based, at least in part, on the classification of the measured carbon isotope value of the *cannabis* sample, or the classification of the below-threshold measured carbon isotope value of the *cannabis* sample.

In some embodiments, the one or more threshold criteria are calculated based, at least in part, on the carbon isotope value of a leaf or plant tissues ($\delta^{13}C_{plant}$) as $\delta^{13}C_{plant} = \delta^{13}C_{air} - a - (b-a) \times c_i/c_a$, where a (4.4‰) and b (27‰) are constants representing the diffusion fractionation against $^{13}CO_2$ and the net fractionation against $^{13}CO_2$ during photosynthesis, respectively, and $c_i/c_a$, is the ratio of intercellular to ambient $CO_2$ levels inside and outside of a leaf or plant tissue.

In some embodiments, the probability density function is calculated using a Bayesian approach describing a known distribution of the authentic material carbon isotope values. In further embodiments, the known distribution of the authentic material carbon isotope values is for authentic material cultivated indoors. In further embodiments, the known distribution of the authentic material carbon isotope values is for authentic material cultivated outdoors.

Also disclosed is a method for determining a *cannabis* cultivation condition comprising obtaining a carbon isotope value of a *cannabis* sample and executing on a processor one or more modules to perform the following steps of classifying the carbon isotope value of the *cannabis* sample against one or more threshold criteria relating to a likelihood a cultivation condition has occurred, evaluating whether the carbon isotope value is above or below the one or more threshold criteria, further classifying a below-threshold carbon isotope value by accessing a database of authentic material isotope values and comparing a probability density function describing the authentic material isotope values, and, based on the comparison, determining a below-threshold likelihood ratio that the below-threshold carbon isotope values is consistent with the likelihood the cultivation condition has occurred.

In further embodiments, the method further comprises obtaining a carbon isotope value. In further embodiments, the step of obtaining a carbon isotope value of a *cannabis* sample further comprises measuring the stable carbon isotope ratio. In further embodiments, the method includes preparing the *cannabis* sample for measurement of the carbon isotope value. In still further embodiments, the method includes certifying that the cultivation condition has, or has not, occurred based, at least in part, on the classification of the carbon isotope value of the *cannabis* sample, or the classification of the below-threshold carbon isotope value of the *cannabis* sample.

Other embodiments of the systems and methods are also possible.

Figure 1:
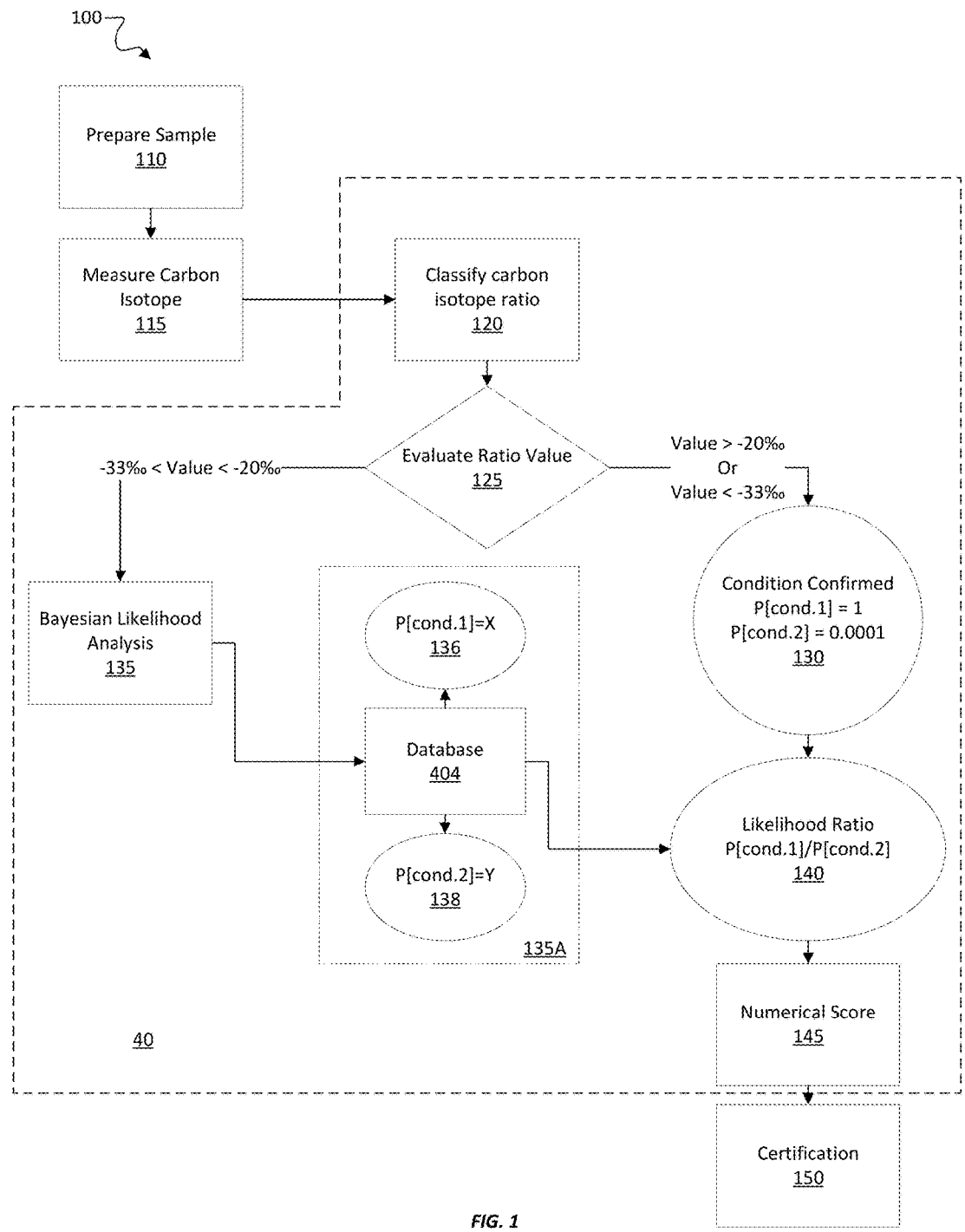
FIG. 1 is a schematic flow diagram illustrating a method for creating and validating a *cannabis* certification in accordance with the disclosure.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

In general, some embodiments of the disclosed method 100 for certifying a cultivation condition may include the steps as described below and with reference to FIG. 1. First, at 110 a *cannabis* sample is prepared for stable carbon isotope ratio analysis.

Second, at 115, the stable carbon isotope ratio of the sample is measured, for example using a flash elemental analyzer 302 coupled to an isotope ratio mass spectrometer 304, and the carbon isotope value of the sample is expressed on an accepted scale.

As indicated schematically on FIG. 1, the next steps are performed with use of computational portion 40. As indicated schematically in FIG. 2, computational portion 40 may include, among other things, a processor 402 and database 404. As will also be apparent to those of ordinary skill in the art, computational portion 40 may provide for interaction with a user on a computer having a display device (e.g., a LED (light emitting diode), a CRT (cathode ray tube) or LCD (liquid crystal display) monitor) for displaying information to the user and a keyboard and a pointing device (e.g., a touch screen, a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

In addition, computational portion 40 may include a back-end component (e.g., as a data server), or a middleware component (e.g., an application server), or a frontend component (e.g., a client computer having a graphical user interface or a Web browser through which a user may interact with an implementation of the subject matter described herein), or any combination of such back-end, middleware, or frontend components. The components of the system may be interconnected by any form or medium of digital data communication (e.g., a communication network). Examples of communication networks include a local area network ("LAN"), a wide area network ("WAN"), and the Internet.

Embodiments of computational portion 40 may include clients and servers. A client and server are generally remote from each other and typically interact through a communication network. The relationship of client and server arises by virtue of computer programs running on the respective computers and having a client-server relationship to each other.

Additionally, processor 402 may be able to operate autonomously or collaboratively based on programming parameters and the communication network to include a peer-to-peer relationship, communications and decision making between multiple peers independently or under the instruction of a client-server system.

Computer program instructions may be provided to processor 402, which may be part of a general purpose computer, special purpose computer, or other programmable data processing apparatus to produce a machine, such that the instructions, which execute via processor 402 implement the functions/acts specified on the schematic illustration in FIG. 1 as follows.

Resuming with the third step, at 120, the sample's carbon isotope value is classified using a theoretical model and threshold concept to evaluate, at 125, a desired cultivation condition of the sample to a desired level of certainty. Thus, this step 120 either determines, at 130, that the *cannabis* sample was cultivated using the desired cultivation condition (e.g., P[cond.1]=indoor cultivation) with the desired reliability and, conversely, that the opposite reciprocal cultivation condition (e.g., P[cond.2]=outdoor cultivation) is unlikely, or results in a requirement, at 135, that the *cannabis* sample be further evaluated for the likelihood that it was cultivated with the desired cultivation condition.

Fourth, for *cannabis* samples not classified as using the desired cultivation condition in steps 120, 125, further evaluation of the measured carbon isotope value is then processed, at 135, using a Bayesian likelihood ratio concept, by comparing the observed carbon isotope value of the *cannabis* sample with observations of a database 404 set of authenticated *cannabis* observations, as indicated at 135A. For example, the cultivation condition being evaluated could be whether the *cannabis* was cultivated indoors, and thus, the probability density function for indoor cultivation (e.g., P[cond.1]=X) is evaluated at 136 and the probability density function for outdoor cultivation (e.g., P[cond.2]=Y) is evaluated at 138. As a result, after step 130, and if necessary, step 135-135A, there is a determination, at 140, of whether the desired cultivation condition was used and the associated likelihood that this determination is correct.

In a fifth step, a translation of the measured carbon isotope value to a numerical score, at 145, that represents the degree to which the desired cultivation condition was associated with the determined cultivation condition (e.g., indoor air). Negative scores indicate outdoor cultivation. A score of zero indicates equal likelihood of either indoor or outdoor cultivation. A positive score indicates indoor cultivation. The more positive the numerical score, the greater the extent of indoor air used for that plant's growth.

In a sixth step, for numerical scores in step 145 that verify the desired cultivation condition was used, a certification can be issued at 150 (e.g., using certification portion 50). The certification is designed to meet any state, or other, requirements that the *cannabis* was cultivated using the desired cultivation condition.

Figure 2:
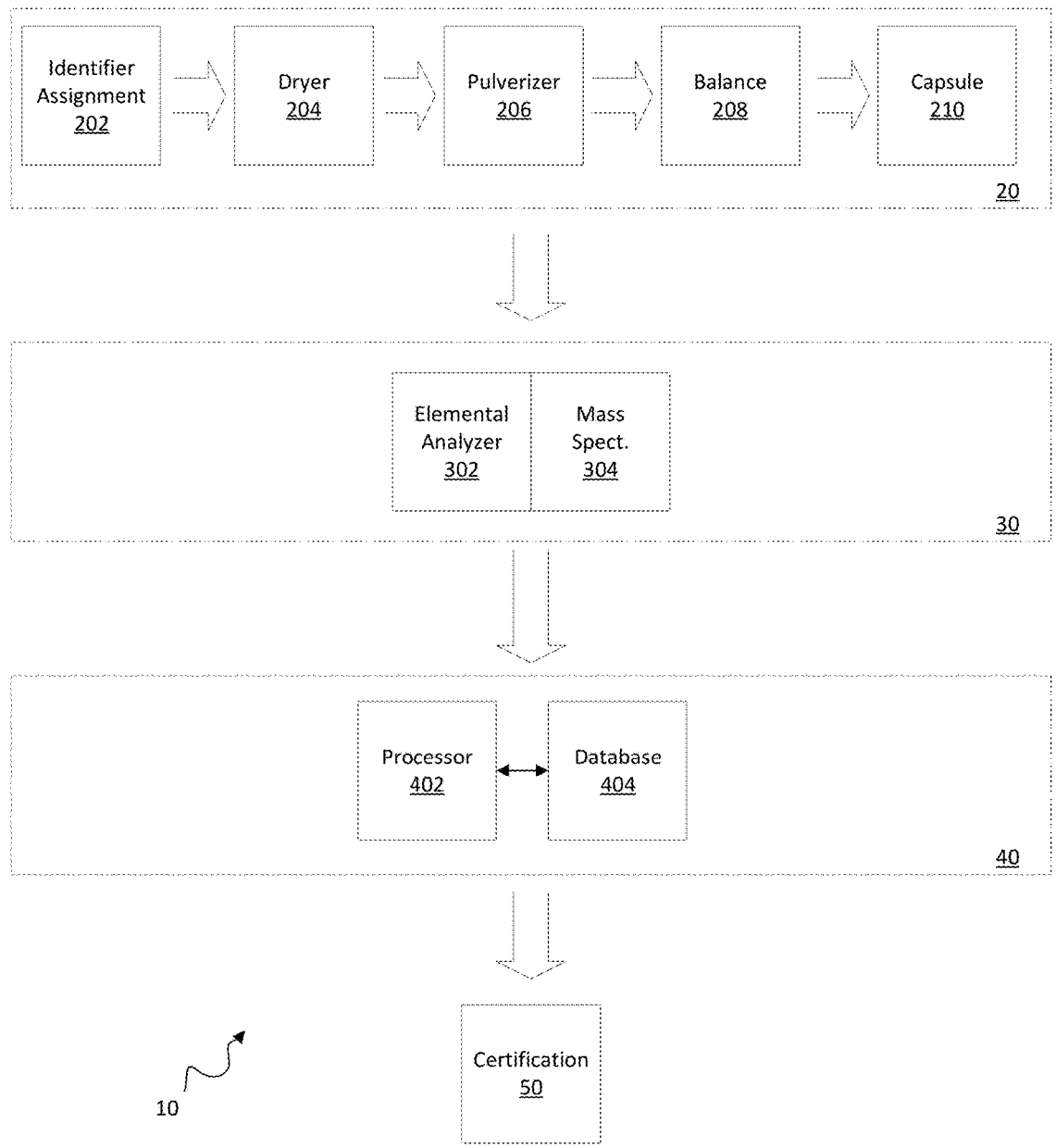
FIG. 2 is a schematic illustration of a certification system in accordance with the disclosure.

FIG. 2 is a schematic illustration of a cultivation certification system in accordance with the disclosure. As shown schematically, system 10 may generally comprise a sample preparation portion 20, an isotope measurement portion 30, a computational portion 40, and a certification portion 50. The various portions 20, 30, 40, and 50, may be collocated in one location, but need not be and embodiments with distributed locations are also possible.

Sample preparation portion 20 is where a *cannabis* sample is prepared for measurement, analysis, and certification as described herein with reference to step 110. Generally, the preparation of a biological tissue for carbon isotope analysis is a routine procedure as is known to those skilled in the art. For example, an identifier assignment portion 202 may assign a unique identifier to each *cannabis* sample received for analysis and/or for cultivation interpretation. The unique identifier is used, among other things, to ensure a verifiable "chain-of-custody" for the sample and "follows" the sample throughout the preparation, measurement, and analysis processes described herein.

Next, the uniquely identified sample may be dried in a dryer 204. For example, in some embodiments, *cannabis* samples may be dried in a 50° C. oven for 48 hours. Other drying procedures are also possible.

After drying, the sample may be pulverized in a pulverizer 206. For example, in some embodiments, 100-200 mg of dried *cannabis* material may be pulverized with a ceramic mortar and pestle until the sample is ground and homogenized. Other pulverizing procedures are also possible.

In some embodiments, the pulverized samples may be stored for later analysis. For example, using 7.6×7.6 cm weigh paper (as sold by VWR, Radnor, Pa.) the pulverized sample may be transferred to a clean 4-ml glass vials (as sold by VWR, Radnor, Pa.) and stored in a cool, dry place until needed for further analysis. Other storage procedures are also possible.

Next, a desired mass of sample *cannabis* material may be measured, for example, with a balance 208 (such as a microbalance sold by Sartorius, Goettingen, Germany). For example, in some embodiments, 300-400 μg of pulverized *cannabis* material may be measured out into an appropriate container or capsule 210. For example, in some embodiments, capsule 210 may comprise a 3.5×5 mm tin capsule (as sold by Costech Analytical, Inc., Valencia, Calif.). The capsule 210 may be sealed by folding or other means to prevent the loss of sample prior to analysis. Other encapsulation procedures are also possible.

After encapsulation, the samples may again be stored until further analysis is desired. Storage is again performed in a manner that preserves the unique identifier and verifiable chain-of custody. For example, the weighed samples may be stored in a plastic tray with numbered wells. Other storage procedures are also possible.

As disclosed herein, once samples are prepared, isotopes may be measured in isotope measurement portion 30 and discussed above with reference to step 115. For example, the stable carbon isotope ratio of a *cannabis* sample may be determined using a flash elemental analyzer 302 coupled to an isotope ratio mass spectrometer 304. The result is the carbon isotope value of a *cannabis* sample expressed on an internationally accepted scale. This measurement can be completed in a number of different ways on any of a number of different commercially available isotope ratio mass spectrometers 304, for which there are a range of models from various manufacturers.

For example, the procedures to measure a carbon isotope value for a *cannabis* sample may be as follows. First, load a weighed capsule containing a sample into a zero-blank autosampler fitted with a 50-sample carousel (such as an autosampler sold by Costech Analytical, Inc., Valencia, Calif.) attached to a Costech ESC 4010 elemental analyzer 302 interfaced via a ConFlo (such as one sold by Thermo Scientific, Waltham, Mass.) to a MAT 253 (such as one sold by Thermo Scientific, Waltham, Mass.) isotope ratio mass spectrometer 304. Once loaded, the samples may be analyzed using established standard operating procedures for the above-identified types of devices.

In some embodiments, for control purposes it may be desirable to analyze each sample in duplicate alongside a set laboratory reference materials (RMs), which had previously been calibrated to the international carbon isotope scale (VPDB). For example, a set of three RMs may be used. RMs may include two primary laboratory reference materials for stretch-shift normalization and a secondary laboratory reference material for quality control.

After analysis, a carbon isotope value is reported in "delta" notation:

$$\delta^{13}C = [(R_{sample}/R_{standard}) - 1],$$

where R represents the $^{13}C/^{12}C$ abundance ratio, and $R_{sample}$ and $R_{standard}$ are the ratios in the sample and standard, respectively.

After the carbon isotope value is measured and quality control checked, a cultivation condition may be determined, as discussed above with reference to steps 120, 125, 130, 135, 135A, 140, and 145, using computational portion 40 which may comprise any suitable processor 402 (e.g., a desktop, laptop, or other computer) in communication with database 404. In the following example, the cultivation condition to be determined is whether the *cannabis* sample was grown with indoor cultivation. However, other cultivation conditions may also be determined in a similar manner.

First, the carbon isotope value of the *cannabis* sample is evaluated, as discussed with reference to step 125, in comparison to the upper and lower limits of carbon isotope values that are theoretically possible for outdoor cultivated *cannabis* plants and for indoor cultivated *cannabis* plants. There are two possible outcomes of these calculations as applied to the decision tree analysis: (1) virtually certain that the *cannabis* was indoor cultivated (e.g., with 99-100% reliability), or (2) it is possible that *cannabis* was either outdoor cultivated or indoor cultivated (e.g., <99% reliability).

In the publications G. D. Farquhar, et al., *On the Relationship Between Carbon Isotope Discrimination and the Intercellular Carbon Dioxide Concentration in Leaves*, 9 Aust. J. Plant Physiol., 121-37 (1982) and G. D. Farquhar, et al., *Carbon Isotope Discrimination and Photosynthesis,*

40 Annual Rev. Plant Physiol. Plant Mol. Biol., 503-37 (1989), each of which is incorporated herein by reference, Farquhar and colleagues developed the theory to explain observed variations in the carbon isotope values of C3-photosynthesis plants, which includes all *Cannabis* sp. That theory has been extensively tested and is accepted. Carbon isotope values vary in C3 plants for two primary reasons: (1) variations in the carbon isotope value of the $CO_2$ (air) in the growth environment ($\delta^{13}C_{air}$) and (2) because of variations in the ratio of intercellular to ambient $CO_2$ levels inside and outside of a leaf ($c_i/c_a$). Using Farquhar's original terminology and equation, the carbon isotope value of a leaf or plant tissues ($\delta^{13}C_{plant}$) can be predicted as:

$$\delta^{13}C_{plant} = \delta^{13}C_{air} - a - (b-a) \times c_i/c_a \quad \text{(Equation 1)},$$

where a (4.4‰) and b (27‰) are constants representing the diffusion fractionation against $^{13}CO_2$ and the net fractionation against $^{13}CO_2$ during photosynthesis, respectively.

Predicting the theoretical ranges of carbon isotope values of *cannabis* requires an understanding of possible ranges in the carbon isotope value of the $CO_2$ in the growth environment ($\delta^{13}C_{air}$) and possible ranges in the ratio of intercellular to ambient $CO_2$ levels ($c_i/c_a$). Whenever plants are grown with indoor cultivation, leaf photosynthesis consumes $CO_2$ within these enclosed spaces, which must then be replenished if plants are to continue to grow. The cultivation $CO_2$ within an indoor facility can typically come from at least one of five possible sources: (a) outside atmospheric air, (b) commercially available $CO_2$ generators supplementing outside atmospheric $CO_2$, (c) external combustion sources (e.g., power generations, furnaces, boilers, etc.) supplementing outside atmospheric $CO_2$, (d) commercially available tank or bottled $CO_2$ or frozen $CO_2$ (i.e., dry ice) supplementing outside atmospheric $CO_2$, or (e) biological respiratory processes, such $CO_2$ from decomposing matter, soils, humans, and plants.

The $CO_2$ surrounding a plant is used for photosynthesis, which is converted into the organic carbon in plants. For plants grown with outdoor cultivation, the source of $CO_2$ is the atmosphere. For plants grown with indoor cultivation, the source of the $CO_2$ is typically a mix of atmospheric and supplied sources. The naturally occurring carbon isotope values of $CO_2$ in outside atmospheric air range from −9‰ to −8‰. Commercial $CO_2$ generators produce $CO_2$ by combusting natural gas that has naturally occurring carbon isotope values of −80‰ to −30‰, resulting in production of $CO_2$ with similar carbon isotope values, making the $\delta^{13}C$ values of $CO_2$ produced from commercial $CO_2$ generators more negative and distinguishable from naturally occurring atmospheric $CO_2$. Commercial $CO_2$ generators are the most common approach for commercial indoor cultivation. External combustion sources combust coal or natural gas to produce $CO_2$. This $CO_2$ is cleaned of residual particulates and transported to the indoor growth facility. The carbon isotope value of $CO_2$ generated from combustion of fossil fuels (e.g., coals and natural gas) are lower than −25‰, again making the $\delta^{13}C$ values of $CO_2$ produced from the combustion of fossil fuels more negative and distinguishable from naturally occurring atmospheric $CO_2$. Other sources of $CO_2$ include bottled $CO_2$, available as high-pressure cylinders (such as those commercially supplied by suppliers such as AirGas, Linde, and Praxair) or low-pressure cylinders (such as those used in the soft drink industry). Commercially bottled $CO_2$ exhibits a range of carbon isotope values, reflecting biological sources (−28‰ to −24‰) and geological sources (−60‰ to −30‰ and −5‰ to +1‰), again making the $\delta^{13}C$ values of bottled $CO_2$ more negative and distinguishable from naturally occurring atmospheric $CO_2$. Lastly, the carbon isotope values of biologically derived $CO_2$ range from −30‰ to −15‰, depending on the extent of C3 and C4 photosynthetic sources contributing to the respiration ending up as $CO_2$ in the atmosphere. The $\delta^{13}C$ values of biologically derived $CO_2$ are more negative and distinguishable from naturally occurring atmospheric $CO_2$.

Under current conditions, commercially available $CO_2$ generators and commercially available bottled $CO_2$ tanks are the most viable options to provide adequate $CO_2$ levels critical to promoting indoor cultivation. Less commonly, open glasshouse windows combined with high velocity fans (i.e., to draw in atmospheric $CO_2$), but without $CO_2$ generators, may still be found in some older facilities. Lastly, the fluxes of $CO_2$ derived from biological sources in an enclosed setting are small and, thus, have a limited capacity to serve as a contributing $CO_2$ source.

Turning now to the intercellular $CO_2$ concentration within a leaf ($c_i$), it is always less than the $CO_2$ concentration in the ambient air outside of a leaf ($c_a$), as photosynthesis reduces cellular $CO_2$, and thus, $c_i/c_a$ is always less than 1. On average, the $c_i/c_a$ of a C3 plant, such as *cannabis*, is 0.7. A sensitivity analysis found that the natural range of $c_i/c_a$ is 0.50 to 0.81. Within natural settings, hanging gardens produced leaves with the most negative carbon isotope values, averaging −31.1‰ for six herbaceous plants in an extremely moist and shaded vegetation; this carbon isotope value reflects a $c_i/c_a$ of 0.82 when the atmospheric and leaf carbon isotope values are inserted in Equation 1 (above). In contrast, very water stressed plants result in a naturally occurring $c_i/c_a$ of 0.50.

Based on Equation 1 (above), the range of carbon isotope values of $CO_2$ in air, and the $c_i/c_a$ described in the previous paragraph, the lower and upper limits of carbon isotope values of *cannabis* are calculated (e.g., using processor 402) as follows: (a) cultivated outdoors (Table 1), (b) cultivated indoors using a commercial $CO_2$ generator (Table 2), (c) cultivated indoors using bottled $CO_2$ of biological origin (Table 3), (d) cultivated indoors using bottled $CO_2$ that is of fossil fuel origin (Table 4), (e) cultivated indoors using bottled $CO_2$ that is of geothermal origin (Table 5), and (f) cultivated indoors at a $CO_2$ level typical of indoor cultivation practices (1.500 ppm) using $CO_2$ from a commercial $CO_2$ generator (Table 6).

TABLE 1

The calculated theoretical lower and upper limits for carbon isotope values of cannabis cultivated outdoors. For these calculations, a photosynthetic drawdown of $CO_2$ around the plants of 10 ppm from an atmospheric $CO_2$ value of 400 ppm are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −9 | | −24.0 |
| $c_i/c_a = 0.50$ | | −8 | −24.0 |
| $c_i/c_a = 0.81$ | −9 | | −31.7 |
| $c_i/c_a = 0.81$ | | −8 | −30.7 |

TABLE 2

The calculated theoretical lower and upper limits for carbon isotope values of cannabis cultivated indoors using a commercial $CO_2$ generator. For these calculations, an atmospheric $CO_2$ around the plants of 600 ppm and an outside background of $CO_2$ with values of 400 ppm and −8.3‰ are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −32 |  | −47.9 |
| $c_i/c_a = 0.50$ |  | −15 | −31.2 |
| $c_i/c_a = 0.81$ | −32 |  | −54.9 |
| $c_i/c_a = 0.81$ |  | −15 | −38.2 |

TABLE 3

The calculated theoretical lower and upper limits for carbon isotope values of cannabis cultivated indoors using bottled $CO_2$ of biological origin. For these calculations, an atmospheric $CO_2$ around the plants of 600 ppm and an outside background of $CO_2$ with values of 400 ppm and −8.3‰ are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −15 |  | −30.6 |
| $c_i/c_a = 0.50$ |  | −14 | −29.2 |
| $c_i/c_a = 0.81$ | −15 |  | −37.6 |
| $c_i/c_a = 0.81$ |  | −14 | −36.2 |

TABLE 4

The calculated theoretical lower and upper limits for carbon isotope values of cannabis cultivated indoors using bottled $CO_2$ of fossil fuel origin. For these calculations, an atmospheric $CO_2$ around the plants of 600 ppm and an outside background of $CO_2$ with values of 400 ppm and −8.3‰ are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −26 |  | −41.2 |
| $c_i/c_a = 0.50$ |  | −16 | −31.2 |
| $c_i/c_a = 0.81$ | −26 |  | −48.2 |
| $c_i/c_a = 0.81$ |  | −16 | −38.2 |

TABLE 5

The calculated theoretical lower and upper limits for carbon isotope values of cannabis cultivated indoors using bottled "$^{13}C$ heavy" $CO_2$ of geothermal origin. For these calculations, an atmospheric $CO_2$ around the plants of 600 ppm and an outside background of $CO_2$ with values of 400 ppm and −8.3‰ are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −7 |  | −22.9 |
| $c_i/c_a = 0.50$ |  | −5 | −20.9 |
| $c_i/c_a = 0.81$ | −7 |  | −29.9 |
| $c_i/c_a = 0.81$ |  | −5 | −27.9 |

TABLE 6

The calculated theoretical lower and upper limits for carbon isotope values of cannabis cultivated indoors using an elevated $CO_2$ level typical of indoor commercial cultivation practices of 1,500 ppm $CO_2$ with $CO_2$ supplied using a commercial $CO_2$ generator. For these calculations, an atmospheric $CO_2$ around the plants of 1,500 ppm and an outside background of $CO_2$ with values of 400 ppm and −8.3‰ are assumed.

| Condition | Lower limit $\delta^{13}C_{air}$, ‰ | Upper limit $\delta^{13}C_{air}$, ‰ | Predicted $\delta^{13}C_{plant}$, ‰ |
|---|---|---|---|
| $c_i/c_a = 0.50$ | −61 |  | −76.6 |
| $c_i/c_a = 0.50$ |  | −24 | −39.9 |
| $c_i/c_a = 0.81$ | −61 |  | −83.6 |
| $c_i/c_a = 0.81$ |  | −24 | −46.9 |

As evident from Tables 1-6, and indicated at step 125, whenever the measured carbon isotope value of a *cannabis* sample is less than −32‰, it is virtually certain that the *cannabis* sample was cultivated indoors (99-100% probability). As most *cannabis* cultivated indoors in commercial settings today utilize $CO_2$ generators, implementation of the herein-described systems and methods has a very high likelihood of being able to detect (and verify and certify) an indoor cultivated *cannabis* sample on the basis of carbon isotope value analysis of a bulk leaf or flower alone. However, for *cannabis* samples with a carbon isotope value greater than −32‰ and less than −24‰, the below-described additional steps are used to distinguish *cannabis* cultivated indoors using old production methods versus *cannabis* cultivated outdoors in either shaded or sunny conditions.

Figure 3:
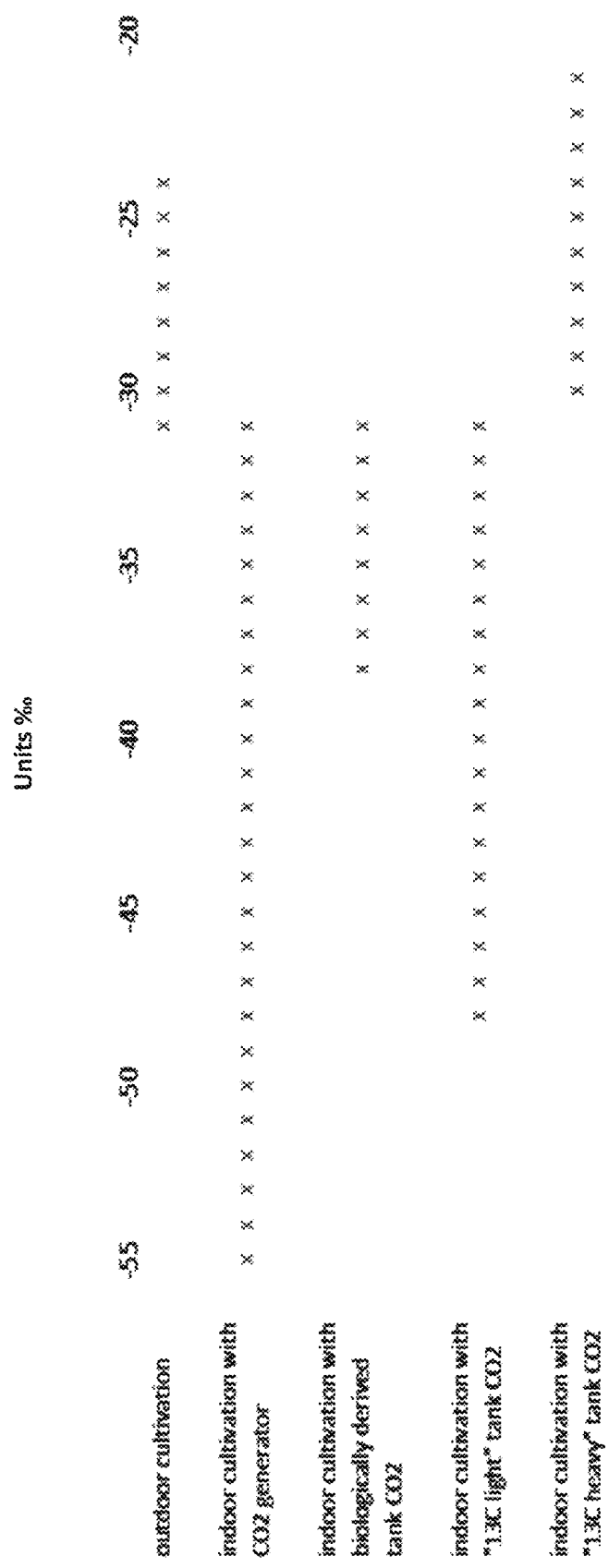
FIG. 3 is a plot of predicted carbon isotope values of indoor cultivation of *cannabis* versus outdoor cultivation of *cannabis* in accordance with the disclosure.

The predicted ranges of *cannabis* carbon isotope values are compared in FIG. 3. In accordance with disclosed embodiments, the only theoretical overlap in carbon isotope values for *cannabis* grown with outdoor cultivation versus *cannabis* grown with indoor cultivation using a $CO_2$ generator will occur at a carbon isotope value of −31‰, as indoor cultivated plants under extreme water stress and outdoor cultivated plants under extremely moist and shaded conditions are predicted to have the same carbon isotope values. The same consistent pattern with minimal carbon isotope value overlap will occur when *cannabis* is also cultivated indoors using respired $CO_2$, bottled $CO_2$ of biological origin, or bottled $CO_2$ that is of fossil fuel origin. It is only when *cannabis* is cultivated indoors using bottled $CO_2$ of geothermal origin that there is overlap in the expected carbon isotope values of plants cultivated outdoors.

As discussed above, and indicated at step 125, for *cannabis* samples with a carbon isotope value of greater than −32‰ and less than −24‰, the below-described additional steps (and indicated at steps 135, 135A) may be employed to further evaluate the sample. In some embodiments, computational portion 40 employs a Bayesian likelihood ratio analysis (at step 135) to compare the measured carbon isotope value of the *cannabis* sample with a reference data set of authenticated observations of the carbon isotope values of *cannabis*.

As indicated at step 135A, part of the analysis involves comparison with a reference data set of *cannabis* that is a compilation of observations of the carbon isotope values of plants documented to have been cultivated indoors versus outdoors. Such a reference data set may be stored, for example, in database 404. As one example of a reference data set, the present applicants have assembled a *cannabis* reference data set containing approximately 800 observations. In accordance with the disclosure, the reference data set may be expanded and revised as additional authentic observations are obtained from medical *cannabis* cultivators and other sources. Exemplary versions of the reference data set stored in database 404 include the date of observation, and consist of authentic indoor cultivated and outdoor cultivated *cannabis* samples.

Using the reference data set in database 404 containing carbon isotope values and associated cultivation regime, and as indicated at step 136, processor 402 creates a frequency distribution describing the probability distribution of carbon isotope values of *cannabis* cultivated indoors for the range of −33‰ to −20‰. Likewise, as indicated at step 138, processor 402 creates a frequency distribution describing the probability distribution of carbon isotope values of *cannabis* cultivated outdoors for the range of −33‰ to −20‰. Using the observed carbon isotope value of a *cannabis* sample and the two frequency distributions (i.e., for indoor and outdoor cultivation), and as indicated at step 140, processor 402 calculates the likelihood ratio that the *cannabis* sample has been cultivated indoors. For example, the outcome of the calculation may be a likelihood ratio (or odds ratio) of two probabilities where the numerator is the probability that a plant with a specific carbon isotope value has been cultivated indoors and the denominator is the probability that a plant with that same specific carbon isotope value has been cultivated outdoors. In the aforementioned manner, processor 402 yields a likelihood ratio that a given *cannabis* sample has been cultivated in an indoor environment.

In some embodiments, and as indicated at step 145, a computational portion 40 of system 10 may be also employed to generate a numerical score and assign it to each *cannabis* sample that is determined to have been cultivated indoors on the basis of a suitable likelihood ratio, for example, a likelihood ratio of 90:1 or higher. One purpose of this numerical assignment is to provide a quantitative assessment of the average atmospheric $CO_2$ concentration during indoor *cannabis* cultivation. One embodiment for calculating may be as follows.

First, calculate using Equation 1 (above) for the carbon isotope value of $CO_2$ in air ($\delta^{13}C_{air}$), using the measured carbon isotope value of the *cannabis* sample ($\delta^{13}C_{plant}$) and plant, a $c_i/c_a$ value of 0.75, which is typical of well-watered conditions. Next, using the calculated $\delta^{13}C_{air}$ value, convert into its associated average atmospheric $CO_2$ concentration ($[CO_2]_{air}$) using a value of −8.3‰ for background outside atmospheric $CO_2$ ($\delta^{13}C_t$), 400 ppm as the background atmospheric $CO_2$ concentration ($[CO_2]_t$), and a carbon isotope value of −45‰ for the fossil fuel ($\delta^{13}C_{source}$) combusted to elevate indoor atmospheric $CO_2$ levels. A 2-point Keeling plot is then used as the last calculation to provide a quantitative estimate of the indoor $CO_2$ concentration during cultivation. The resulting quantitative estimate may be reported to certification portion 50, as indicated at step 150, with the estimated average $CO_2$ concentration in the indoor cultivation environment in conjunction with the unique *cannabis* sample identifier in order to produce a certificate, or otherwise certify the sample. In addition, the sample data may be archived in suitable storage, such as database 404. Thus, system 10 and the disclosed method may be used to produce a verification or certification that a *cannabis* sample has been, or has not been cultivated indoors. As noted above, other cultivation conditions may also be verified or certified.

Although various embodiments have been shown and described, the present disclosure is not so limited and will be understood to include all such modifications and variations are would be apparent to one skilled in the art.

What is claimed is:

1. A *cannabis* cultivation condition determination system comprising:
   an isotope measurement portion for measuring a carbon isotope value of a *cannabis* sample; and
   a computational portion further comprising:
   a processor; and
   a database comprising authentic material carbon isotope values; and wherein the processor is programmed to:
   classify the measured carbon isotope value of the *cannabis* sample against one or more threshold criteria relating to a likelihood a cultivation condition has occurred;
   evaluate whether the measured carbon isotope value is above or below the one or more threshold criteria;
   further classify a below-threshold measured carbon isotope value by comparing a probability density function describing the authentic material carbon isotope values; and,
   based on the comparison, determine a below-threshold likelihood ratio that the below-threshold measured carbon isotope value is consistent with the likelihood the cultivation condition has occurred.

2. The system of claim 1 further comprising:
   a sample preparation portion for preparing the *cannabis* sample for measurement in the isotope measurement portion.

3. The system of claim 1 further comprising: a certification portion configured for certifying that the cultivation condition has, or has not, occurred based, at least in part, on the classification of the measured carbon isotope value of the *cannabis* sample, or the classification of the below-threshold measured carbon isotope value of the *cannabis* sample.

4. The system of claim 1 wherein the one or more threshold criteria are calculated based, at least in part, on the carbon isotope value of a leaf or plant tissues ($\delta^{13}C_{plant}$) as:

$$\delta^{13}C_{plant}=\delta^{13}C_{air-a-(b-a)\times c_i/c_a}$$

where a (4.4‰) and b (27‰)) are constants representing the diffusion fractionation against $^{13}CO_2$ and the net fractionation against $^{13}CO_2$ during photosynthesis, respectively, and $c_i/c_a$, is the ratio of intercellular to ambient $CO_2$ levels inside and outside of a leaf or plant tissue.

5. The system of claim 1 wherein the probability density function is programmed to be calculated using a Bayesian approach describing a known distribution of the authentic material carbon isotope values.

6. The system of claim 5 wherein the known distribution of the authentic material carbon isotope values is for authentic material cultivated indoors.

7. The system of claim 5 wherein the known distribution of the authentic material carbon isotope values is for authentic material cultivated outdoors.

8. A method for determining a *cannabis* cultivation condition comprising:
   obtaining a carbon isotope value of a *cannabis* sample; and
   executing on a processor one or modules to perform the following steps:
   classifying the carbon isotope value of the *cannabis* sample against one or more threshold criteria relating to a likelihood a cultivation condition has occurred;
   evaluating whether the carbon isotope value is above or below the one or more threshold criteria;
   further classifying a below-threshold carbon isotope value by accessing a database of authentic material isotope values and comparing a probability density function describing the authentic material isotope values; and, based on the comparison, determining a below-threshold likelihood ratio that the below-threshold carbon isotope value is consistent with the likelihood the cultivation condition has occurred.

9. The method of claim 8 wherein the step of obtaining a carbon isotope value of a *cannabis* sample further comprises determining a carbon isotope value.

10. The method of claim 9 wherein the step of determining a carbon isotope value of a *cannabis* sample further comprises measuring the carbon isotope value.

11. The method of claim 10 further comprising:
preparing the *cannabis* sample for measurement of the carbon isotope value.

12. The method of claim 8 further comprising:
certifying that the cultivation condition has, or has not, occurred based, at least in part, on the classification of the carbon isotope value of the *cannabis* sample, or the classification of the below-threshold carbon isotope value of the *cannabis* sample.

13. The method of claim 8 wherein the one or more threshold criteria are calculated based, at least in part, on the carbon isotope value of a leaf or plant tissues ($\delta^{13}C_{plant}$) as:

$$\delta^{13}C_{plant} = \delta^{13}C_{air} - a - (b-a) \times c_i/c_a,$$

where a (4.4‰) and b (27‰) are constants representing the diffusion fractionation against $^{13}CO_2$ and the net fractionation against $^{13}CO_2$ during photosynthesis, respectively, and $c_i/c_a$, is the ratio of intercellular to ambient $CO_2$ levels inside and outside of a leaf or plant tissue.

14. The method of claim 8 wherein the probability density function is calculated using a Bayesian approach describing a known distribution of the authentic material isotope values.

15. The method of claim 14 wherein the known distribution of the authentic material isotope values is for authentic material cultivated indoors.

16. The system of claim 14 wherein the known distribution of the authentic material isotope values is for authentic material cultivated outdoors.

* * * * *